United States Patent [19]

Miller et al.

[11] Patent Number: 5,707,859
[45] Date of Patent: Jan. 13, 1998

[54] TWO-DIMENSIONAL MICROCARRIERS FOR ANCHORAGE DEPENDENT CELLS

[75] Inventors: Alain O. A. Miller, Mons, Belgium; Guy De Hollain, Vernouillet, France; Dominique Masquelier, Brussels, Belgium

[73] Assignee: Nunc, A/S, Roskilde, Denmark

[21] Appl. No.: 107,713

[22] PCT Filed: Feb. 18, 1991

[86] PCT No.: PCT/BE91/00012

§ 371 Date: Dec. 1, 1993

§ 102(e) Date: Dec. 1, 1993

[87] PCT Pub. No.: WO92/14814

PCT Pub. Date: Sep. 3, 1992

[51] Int. Cl.$^6$ .............. C12M 1/00; C12N 5/00; C12N 11/06; C12N 11/14

[52] U.S. Cl. .......... 435/283.1; 435/176; 435/179; 435/180; 435/240.23; 435/240.24

[58] Field of Search ............. 435/240.23, 240.24, 435/240.241, 240.243, 178, 180, 283.1, 176, 179

[56] References Cited

U.S. PATENT DOCUMENTS

| | | | |
|---|---|---|---|
| 3,841,969 | 10/1974 | Nicholas et al. | 435/178 X |
| 4,266,032 | 5/1981 | Miller et al. | 435/241 |
| 4,546,083 | 10/1985 | Meyers et al. | 435/240.242 |
| 5,154,808 | 10/1992 | Miyasaka et al. | 435/180 X |
| 5,254,471 | 10/1993 | Mori et al. | 435/240.23 |
| 5,266,476 | 11/1993 | Sussman et al. | 435/240.23 |
| 5,294,763 | 3/1994 | Chamberlain et al. | 219/729 |

FOREIGN PATENT DOCUMENTS

| | | |
|---|---|---|
| 303294 | 2/1989 | European Pat. Off. . |
| 86337 | 11/1987 | Luxembourg . |

OTHER PUBLICATIONS

A. Johansson and V. Nielsen (1979) Develop. biol. Standard, Biosilon R A New Microcarrier, 46, pp. 125–129 (S. Karger, Basel 1980).

*Primary Examiner*—David M. Naff
*Attorney, Agent, or Firm*—Klein & Szekeres, LLP

[57] ABSTRACT

Two-dimensional microcarriers for culture of anchorage dependent cells are formed having two opposed and parallel anchorage surfaces and a thickness so thin that cells attach only to the surfaces and not between the surfaces. Preferably, each of the surfaces is less than about 500 microns in each of its two dimensions, the thickness is not more than about 35 microns, the microcarriers have a shape resulting from the orthogonal or oblique intersection of two parallel planes separated by a distance of not more than 35 microns with a solid cylinder and the microcarriers are made from a hydrophobic polymeric material such as polystyrene, polycarbonate or polyterephthalate. The microcarriers can be microdisks having a density of between 0.90 and 1.10 g/cm$^3$. The anchorage surfaces may be treated to enable cell attachment by applying a thin metallic deposit such as a titanium deposit or by electrical corona discharge. The microcarriers may be transparent to light waves and capable of withstanding sterilization. To form the microcarriers, the surfaces of a thin film of the polymeric material having a thickness of not more than about 35 microns are treated to be suitable for cell attachment, and the film is cut such as with a laser or by punching to provide the microcarriers.

20 Claims, 9 Drawing Sheets

TWO-DIMENSIONAL MICROCARRIERS FOR ANCHORAGE DEPENDENT CELLS

BACKGROUND OF THE INVENTION

The present invention relates to a support for the culture of anchorage dependent cells (ADC's) in the shape of microcarriers of a biocompatible material. It relates moreover to a process for preparing such a support.

The mammalian cells used as such for producing human and veterinary vaccines, for obtaining molecules having a high added value and for other analogous production processes, are generally ADC's: they require a support for their growth. Without support, these cells degenerate and die in suspension.

The mass cultivation is realized the better on an industrial scale as the available attachment surface area is larger with respect to the total volume of the used support. A calculation the surface/volume ratio of different supports shows that this ratio can vary between 1.25 and 150.0 for some actual microcarriers (see M. BUTLER, Growth Limitations in Microcarrier Cultures, in: Advances in Biochemical Engineering/Biotechnology, pages 57 and following, volume 34, Springer Verlag, 1997).

On an industrial scale, it is easier to make microcarriers of a spherical geometry: the microbeads. That is the reason why the user has nowadays the choice between a very large variety of this type of microcarriers (see amongst others, A. SHAHAR et al, Nerve and Muscle Cells on Microcarriers in Culture, in: Advances . . . , op. cit., pages 33 and following, volume 34, 1987).

In spite of all their potentialities, there are only a few examples in the world wherein the ADC's are cultivated in mass on microcarriers. The Roux bottles, the rotating flasks and other "cell factories" remain the most generally used systems.

The reasons underlying this situation, as well as the means to be used in order to put an end to this, were the subject of a detailed study (see A. O. A. MILLER et al., Microbeads and Anchorage-Dependent Eukaryotic Cells: The Beginning of a New Era in Biotechnology, in: "Advances . . . op. cit., pages 73 and followings volume 39, 1989).

Recently, essentially in order to reduce the production costs of substances produced by the ADC's, use has been made of polystyrene spirals and of disks having a thickness of 1.5 mm and a diameter of 6 mm formed by a polypropylene netting coated with a polyester film (see A. KADOURI et al., Polystyrene substratum for bulk culture of anchorage dependent cells, in Cytotechnology, 1: 301–307, 1988; M. NEEMAN et at., Adaptation of Culture Methods for NMR Studies of Anchorage-Dependent Cells, in Magnetic Resonance in Medicine, 7, 236–242, 1988; A. KADOURI et al., Production of Anti-Leukemic Factor from Stroma Cells in a Stationary Bed Reactor on a New Cell Support, in 9th ESACT Meeting, Belgium, pages 327 and following, Butterworths, 1989).

All the hereabove mentioned supports are characterized by a three-dimensional geometry. For many of these supports, even with respect to the microbeads and the thick disks of a woven material, the surface/volume ratio of the support remains unfavourable. Besides, these thick disks made of a netting of a woven material present the drawback of allowing the cells to penetrate and to attach within these disks. These cells can no longer be removed subsequently from their support or with very much difficulties, which represents an important drawback and a loss of dry matter when the cells are cultivated for themselves. As a matter of fact, these disks allow only a culture of cells attached ad vitam to their support, for example for the purpose of secreting a given substance which is collected. In this type of culture, the cell supports are not in suspension.

DETAILED DESCRIPTION OF THE INVENTION

An object of the present invention is to meet the problems posed by the supports according to the prior state of the art, while ameliorating more particularly the surface/volume ratio of the culture support. Preferably, the invention has to enable to detach the cells easily from their supports without damaging the cells, as well as to cultivate them in suspension. It is necessary for the supports according to the invention to be biocompatible. Preferably, they allow to analyse the cells during their growth easily, and their density enables a culture in suspension in the culture medium. Advantageously, there is achieved that the supports resist to the sterilization conditions.

In order to solve these problems, there is provided according to the invention a support for the culture of ADC's in the shape of microcarriers of a biocompatible material, wherein the microcarriers have a two-dimensional geometry and comprise two apposed anchorage surfaces, both of which enable the cells to attach themselves and to develop without any possibility for the cells to penetrate between these two surfaces.

By two-dimensional geometry, there has to be understood that the thickness of these microcarriers tends to become infinitesimal and negligible with respect to the dimensions of the ADC's. This thickness, reduction is such that there is not any possibility for cell growth within the support but only onto the two anchorage surfaces.

According to an embodiment of the invention, the microcarriers have a thickness which is preferably smaller than or equal to 25 microns, and which is very advantageously smaller than or equal to 12 microns.

According to a preferred embodiment of the invention, the microcarriers have a discoidal shape and are in particular disk or spindle-shaped. The expression discoidal indicates, within the scope of the present invention, the family of particles obtained by orthogonal (disks) or oblique (spindles) intersection of two parallel planes at a mutual distance of 35 microns at the most, with a solid cylinder.

According to an advantageous embodiment of the invention, the microcarriers have, in the culture medium, a density comprised between 0.90 and 1.10 g/cm$^3$, and preferably between 1.03 and 1.05 g/cm$^3$. The density of the microcarriers is appropriate in particular in order that the turbulences produced in the fluid serving as culture medium to maintain them in suspension, do not traumatize the attached cells and do not change their viability. When they are too light, the microcarriers will float whereas they will settle to the bottom of the bioreactor when they are too heavy. In order to keep the cells in suspension, the culture medium has therefore to be agitated under such speed conditions that the so-produced shearing forces do not detach the cells by giving them multiple traumatisms.

According to a particular embodiment of the invention, the microcarriers are made of a sterilization-resistant material. This enables to avoid contaminants (bacteries, mycoplasms, yeasts, viruses, etc . . . ) adhering to the microcarriers to develop in the cell culture at the expense of these cells.

According to another embodiment of the invention, the microcarriers are transparent for waves comprised between 400 nm and 1000 nm. By transparency there is understood that in this range of wave lengths, the light traverses the microcarriers without important attenuation of the emerging light beam intensity with respect to the intensity of the incident light beam. An absorption lower than 1% is considered to be fully satisfying.

According to an embodiment of the invention, the microcarriers are made of a polymeric material. As polymeric material, there can for example be considered a polymer containing numerous aromatic groups, and in particular polystyrene. Further, polycarbonate or polyterephthalate can also be considered. Of course, other materials do not have to be excluded and disks of a hydrophilic material for example, such as cellophane or poly-D-hydroxybutyrate, are imaginable. However, they present the drawback of swelling in water, as a consequence of which they may loose their two-dimensional geometry.

According to the invention, it is necessary for the microcarriers to be biocompatible. By biocompatibility, there is to be understood within the meaning of the present invention, that these ADC's are capable to attach themselves onto the surfaces of the microcarriers according to the invention and to multiply thereon.

To this end, it is advantageously provided to coat the two surfaces of the microcarriers according to the invention with a thin metallic deposit. This deposit is advantageously a titanium deposit. However, use can also be made of platinium for example.

The microcarriers according to the invention offer a series of significant advantages with respect to the three-dimensional microcarriers used nowadays.

A simple calculation allows to realize that the total surface of two disks of a negligible thickness, the diameter of which is equal to the one of the sphere wherin they are inscribed ("equatorial" disks), is equal to the outer surface of the sphere (=microbead).

Within the two portions of the sphere obtained in this way above and beneath these two equatorial disks, other disks can be located, the diameter of which decreases as the distance from the equator increases towards the poles. When assuming a thickness of 10 microns for each of the so-created disks and when expressing their surface area as "equivalent equatorial surface", the total surface offered in this way by the disks is 5 to 7 times larger than the outer surface of the sphere.

Of course, in suspension, the random movements of these microdisks as well as the increased thickness resulting from the adhesion of the ADC's, contribute to reduce the total available surface. Nevertheless, this surface remains larger than at least two times the outer surface of the sphere.

Moreover, the reduction of the diameter of the microdisks, for example to 80 microns, allows to use the nozzles developed in the flow cytometry to realize the hydrodynamical focusing. The movement in single file through the beam of the interrogator laser can further be ameliorated by decreasing the freedom degrees of the microdisks as a consequence of their shaping into spindle-shaped supports. Such an approach would allow to implement to the cells anchoraged onto the support the analysis and sorting techniques developed in flow cytometry without any need to detach them previously by means of trypsine or ethylene-diamine tetraacetate (EDTA). The in situ analysis becomes easy and the cellular damages resulting from a trypsine or EDTA treatment are avoided.

According to their thickness, one can think of thin microcarriers, preferably of 1 to 25 microns, or of ultra-thin microcarriers, i.e. having a thickness smaller than 1 micron.

The microdisks according to the invention and having a diameter smaller than 500 microns, have the important advantage that they can be transferred with a pipette and that they can be used without problems in suspended cultures. Although they can also be used in suspension, the microdisks, the diameter of which is of a higher dimension, are rather used in the immobilized cultures due to the fact that they can only be transferred by decanting.

The present invention relates also to a method for manufacturing a support for the culture of ADC's in the shape of microcarriers of a biocompatible material, which method is characterized in that it comprises the step of cutting up a thin or ultra-thin film into microcarriers having a two-dimensional geometry and comprising two apposed anchorage surfaces, both of which enable the cells to attach themselves and to develop without any possibility for the cells to penetrate between these two surfaces, as well as the optional step of pretreating the film to make it biocompatible.

The thin or ultra-thin film can be cut up in any appropriate way according to the nature of the film. Polystyrene films, for example, contain numerous aromatic groups and are suited to be photoablated by means of an excision laser. One can also think of punching the film out into microcarriers, which is particularly advantageous in the case of microcarriers having a large diameter. Notwithstanding the relatively bad quality of this cutting type, it is possible to consider to cut up for example disks of cellophane, which is previously coloured in red with a non-toxic substance, by pyrolysis (argon laser). Other methods can of course possibly also be considered.

In the case wherein the material, the support according to the invention is made of, is not biocompatible by itself, which is the case for example for polystyrene, there has to be provided moreover, before the cutting up step, an appropriate treatment for making this material biocompatible, To this end, the invention provides to apply a thin metallic deposit, in particular a titanium deposit, onto each of the surfaces of the thin film.

A method for vaporizing a thin titanium layer onto the inner surface of a Petri dish is described more particularly in patent LU-A-86337. Other application methods, especially by projection of titanium plasma by means of a magnetron, can also be considered.

The use of thin polystyrene or cellophane disks or spindles coated with a titanium layer onto both surfaces, enables to consider the possibility of electrolytically detaching the cells.

In order to make the thin or ultra-thin film biocompatible, one can also think, according to the invention, of passing an electrical corona discharge through the film.

It has to be noted that, when polystyrene does not resist to a sterilization in an autoclave, it may be sterilized by gamma irradiation. A sterilization by means of alcohol can also be considered.

Tests destined to evaluate the adhesion capacity of ADC's have been performed on disks having a diameter of 8 mm and punched out of polystyrene and cellophane films.

The cells used in these tests are Vero cells which are available on the market and which have been cultivated in Roux bottles, having a surface of 200 cm$^2$, in a humid incubator (37° C., 95% air/5% $CO_2$) in medium 199 (Gibco) enriched with 5% foetal calf serum (Gibco) and containing 100 U penicillin and 0.1 mg streptomycin/ml.

The bottom of the bottles containing the cells is rinsed by means of a PBS solution and the cells are detached by trypsinization (0.5% of Gibco trypsine solution 1/250 containing 0.2% EDTA). This enzymatic digestion of the matrix is carried out until the moment the cells detaching themselves become visible with the naked eye. At that moment, the activity of the enzyme is stopped by adding complete medium. The cells are centrifuged (1000 rpm-centrifuge ECCO type H 6.5) for 10 minutes. After removing the supernatant, the cells are resuspended into a determined volume of medium in order to determine their concentration by using to this end the counting cell of Burker.

Then, 40,000 cells are incubated onto the surface of the microcarriers according to the invention, either or not previously coated with titanium. These microcarriers have been deposited into a multiwell box (24). They are means o on the bottom of the wells by means of a small quantity of glycerol. The observations are realized 24 hours after this inoculation.

Figure 1:
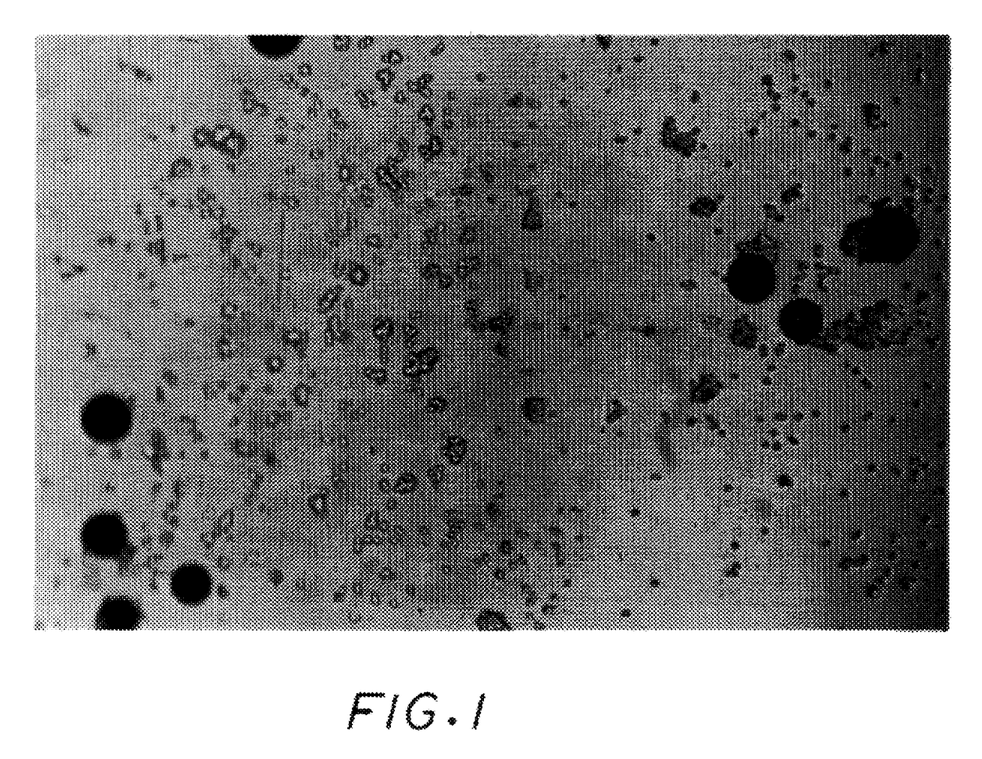
FIGS. 1 to 3 represents microscopic photo of three reference disks, respectively, made of a cellophane quality A film, a cellophane quality B and a polystrene film, and subjected to the Tests later described in this application.
Figure 2:
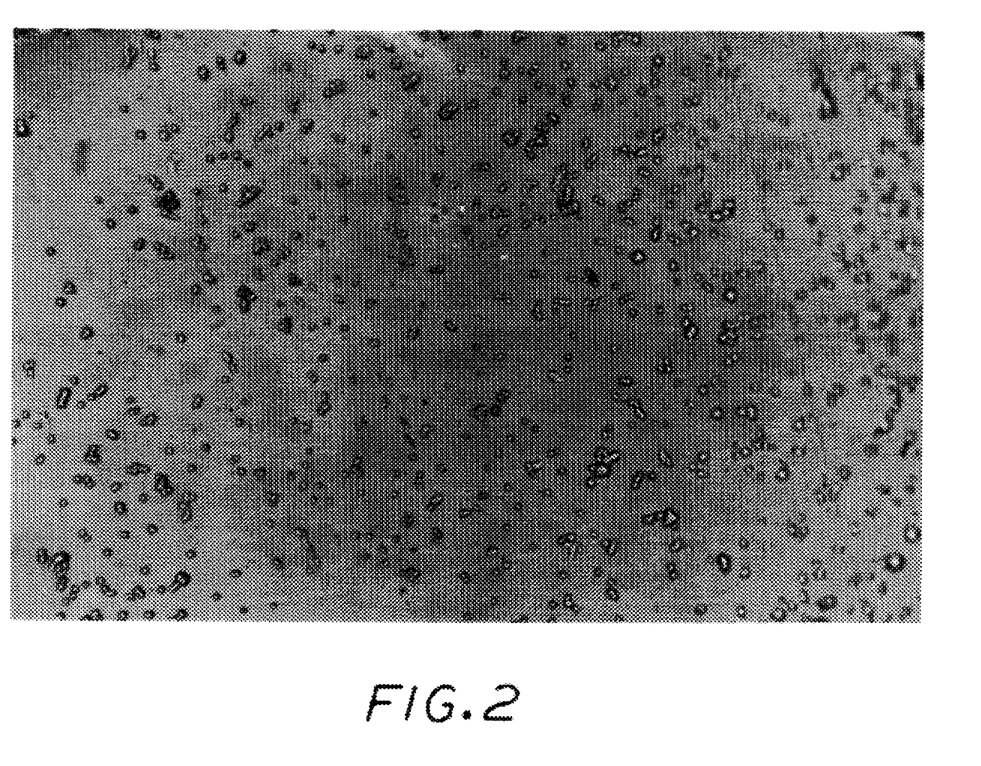
Figure 3:
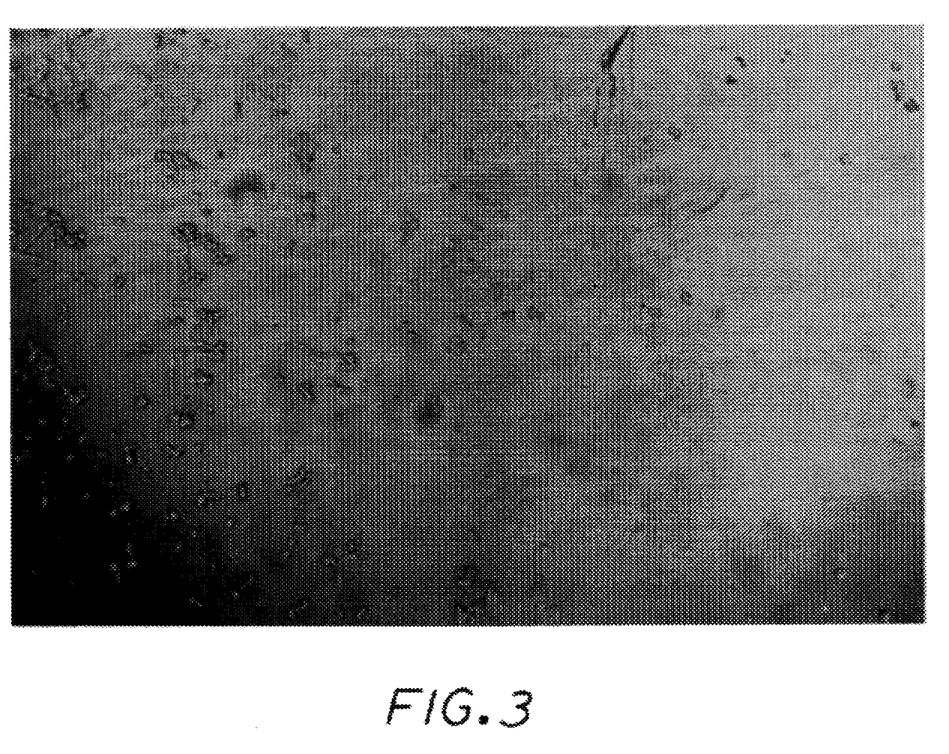
Figure 4:
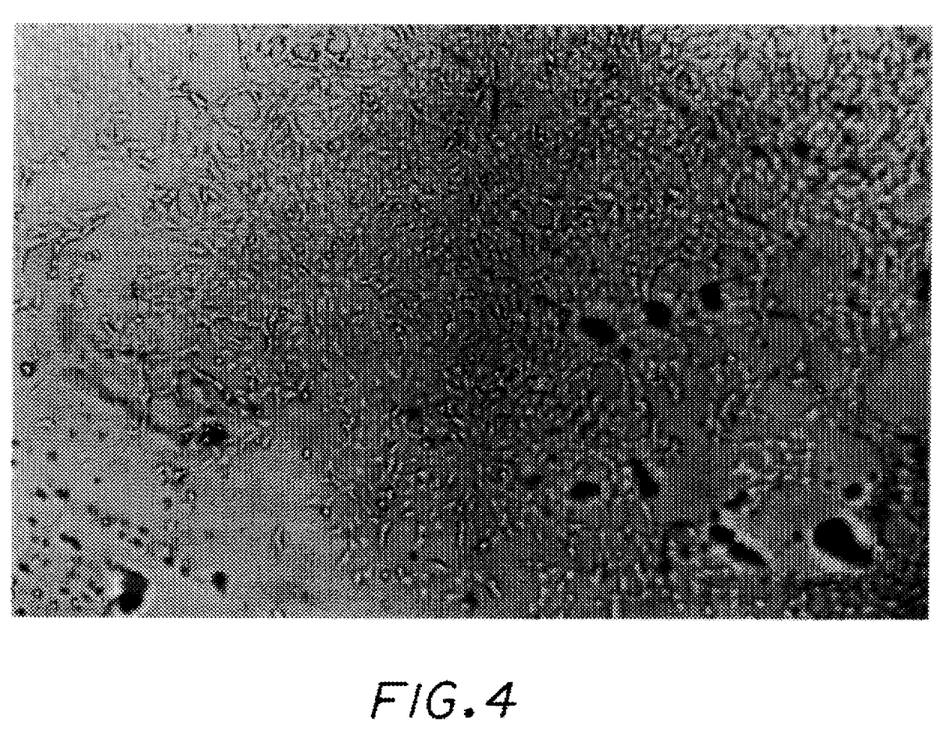
FIGS. 4 to 6 represents similar photos of three disks made of the same films as in FIGS. 1 to 3 but after projection in a magnetron of tinanium plasma onto both their surfaces.
Figure 5:
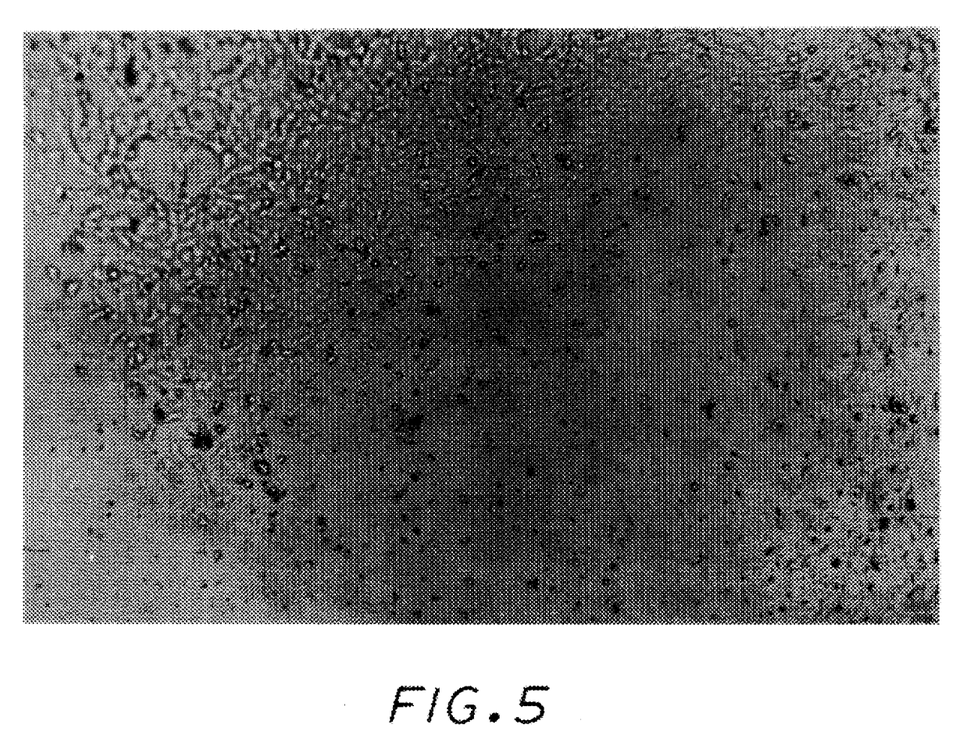
Figure 6:
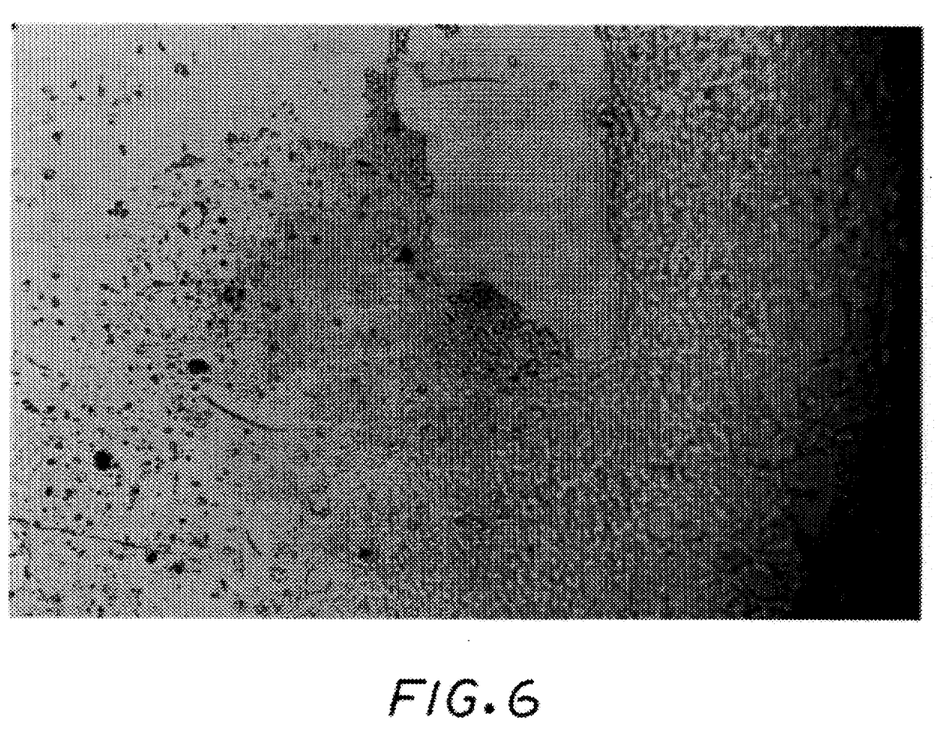
Figure 7:
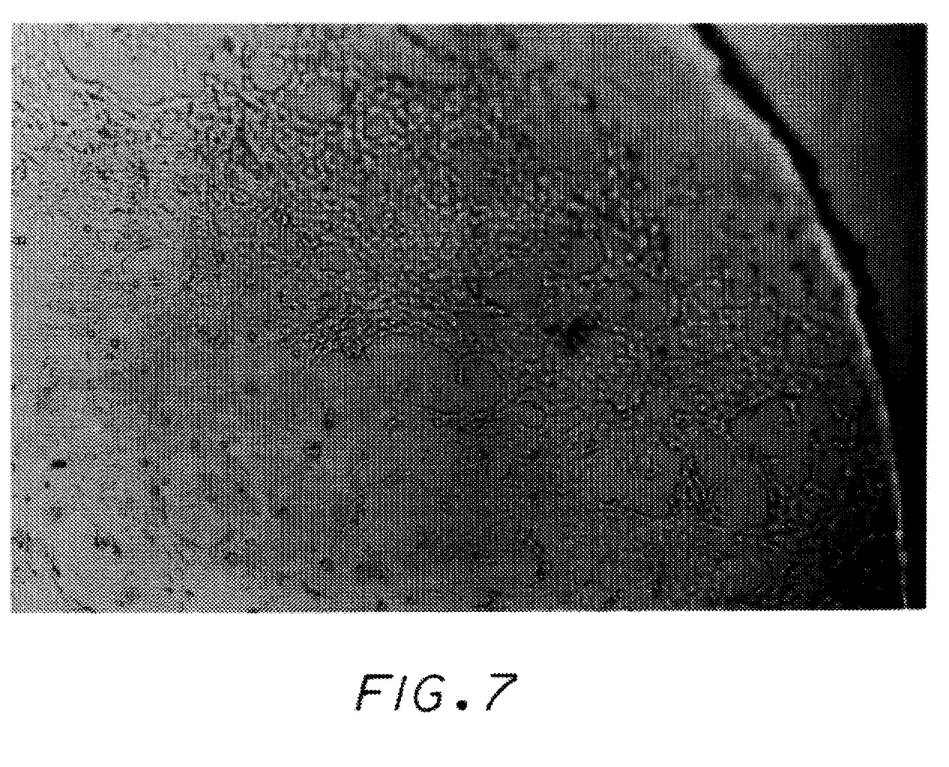
FIGS. 7 to 9 represents similar photos of three disks made of the same films as in FIGS. 1 to 3, but after vaporization of titanium onto both their surfaces.
Figure 8:
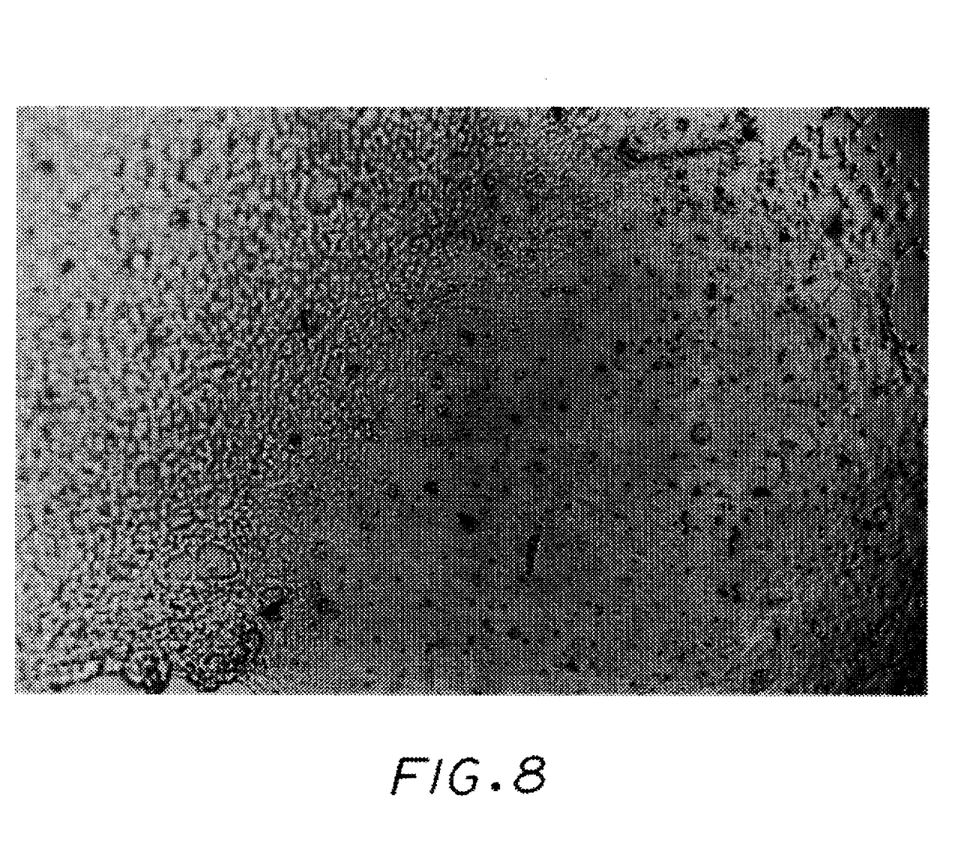
Figure 9:
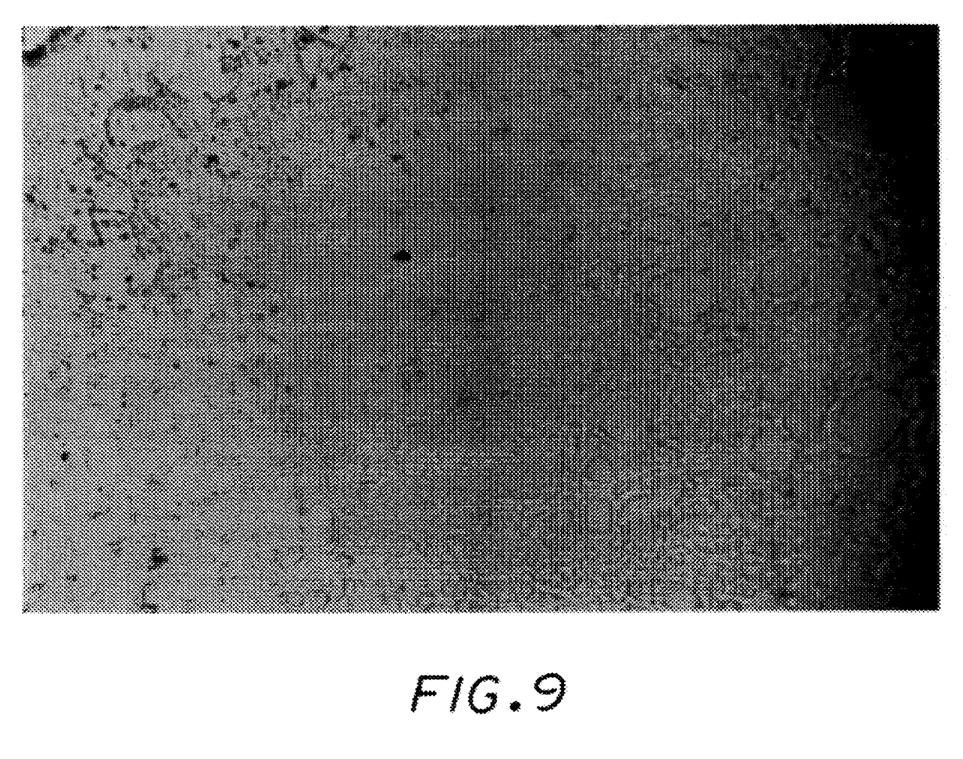

It appears from FIGS. 1–9, that the used disks according to the invention show a cellular efficiency which is far more superior after applying a titanium layer onto both their surfaces.

It is clear that, when the cut up film is made of a material which is biocompatible as such, which may be for example the case for certain cellophane types, a thin titanium layer has no longer to be applied.

A test which is similar to the previous ones, was performed on disks cut up from a polystyrene sheet treated by a corona discharge effect to make it biocompatible. The obtained results are as satisfying as those illustrated in FIGS. 6 and 9.

Tests analogous to the previous ones, were also performed onto human keratinocyte cells and onto diploid fibroblasts of rats, with results which are just as well.

It is clear that other shapes than the shape of discoids could be suitable for the microcarriers. One could consider ellipses, ovals, squares, lozenges, other polygons, etc.

We claim:

1. A support for the suspended culture of anchorage cells comprising two-dimensional microcarriers formed of a hydrophobic, polymeric material, each of the microcarriers comprising a pair of apposed and parallel two-dimensional anchorage surfaces, each of the anchorage surfaces being less than about 500 microns in each of its two dimensions, each of the anchorage surfaces being treated so as to enable the cells to attach thereto, the distance between the two anchorage surfaces being such that the microcarriers each have a thickness of not more than about 35 microns, so that the cells can attach only to the anchorage surfaces and not between the anchorage surfaces, wherein each of the microcarriers has a shape determined by the orthogonal or oblique intersection of two parallel planes with a solid cylinder, the planes being separated by a distance of not more than about 35 microns.

2. The support according to claim 1, wherein the microcarriers have a thickness of not more than about 25 microns.

3. The support according to claim 1, wherein the microcarriers have a thickness of not more than about 12 microns.

4. The support according to claim 1, wherein the microcarriers have a density of between 0.90 and 1.10 g/cm$^3$.

5. The support according to claim 1, wherein the microcarriers have a density of between 1.03 and 1.05 g/cm$^3$.

6. The support according to claim 1, wherein the microcarriers are transparent for light waves.

7. The support according to claim 1, wherein the two apposed anchorage surfaces of the microcarriers are coated with a thin metallic deposit.

8. The support according to claim 7, wherein the metallic deposit is a titanium deposit.

9. The support according to claim 1, wherein the polymeric material is selected from the group consisting of polystyrene, polycarbonate and polyterephthalate.

10. The support according to claim 1, wherein the surfaces of the microcarriers are subjected to a corona discharge so that said surfaces are biocompatible.

11. A method for manufacturing a support for the suspended culture of anchorage dependent cells, said method comprising the steps of:

(a) providing a film having first and second apposed, parallel surfaces and a thickness of not more than about 35 microns;

(b) treating the first and second surfaces of the film so as to enable the cells to attach to the first and second surfaces; and (c) cutting the film into two-dimensional microcarriers, each including two apposed and parallel two-dimensional anchorage surfaces, each of the anchorage surfaces being less than about 500 microns in each of its two dimensions, and the distance between the first and second anchorage surfaces being such that the thickness of each microcarrier is not more than about 35 microns, so that the cells can attach only to the anchorage surfaces and not between the anchorage surfaces, wherein each of the microcarriers has a shape determined by the orthogonal or oblique intersection of two parallel planes with a solid cylinder, the planes being separated by a distance of not more than about 35 microns.

12. The method according to claim 11, wherein the film has a thickness of not more than about 25 microns.

13. The method according to claim 11, wherein the film has a thickness of not more than about 12 microns.

14. The method according to claim 11, wherein the cutting is accomplished by means of a laser.

15. The method according to claim 11, wherein the surfaces of the film are treated by applying a thin metallic deposit to said surfaces.

16. The method according to claim 15, wherein the thin metallic deposit is applied by plasma projection.

17. The method according to claim 15, wherein the thin metallic deposit is applied by vaporization.

18. The method according to claim 15, wherein the thin metallic deposit is a titanium deposit.

19. The method according to claim 11, wherein the surfaces of the film are treated by subjecting said surfaces of said film to an electrical corona discharge.

20. The method according to claim 11, wherein the cutting is accomplished by means of punching.

* * * * *